US00PP17200P2

(12) United States Plant Patent
Jonkers

(10) Patent No.: US PP17,200 P2
(45) Date of Patent: Nov. 7, 2006

(54) ***DIASCIA* PLANT NAMED 'DALA ROSSA'**

(50) Latin Name: *Diascia barberae*
Varietal Denomination: Dala Rossa

(75) Inventor: Johanna B. Jonkers, Andijk (NL)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/269,351

(22) Filed: Nov. 8, 2005

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

PP13,949 P2 * 7/2003 Stemkens ..... Plt./263
PP14,498 P2 * 1/2004 Talmadge ..... Plt./263
PP15,561 P2 * 2/2005 Hoogendoorn ..... Plt./263

OTHER PUBLICATIONS

UPOV ROM GTITM Computer Database, GTI Jouve Retrieval Software 2005/05 Citations for 'Dala Rossa'.*

* cited by examiner

*Primary Examiner*—Wendy Haas
(74) *Attorney, Agent, or Firm*—Jondle & Associates P.C.

(57) ABSTRACT

A new *Diascia* plant particularly distinguished by medium-sized rose pink flowers with reddish markings, medium-green foliage with narrow leaves, and a medium-sized semi-upright, tight, and well-branched plant habit is disclosed.

1 Drawing Sheet

Genus and species: *Diascia barberae.*
Variety denomination: 'Dala Rossa'.

BACKGROUND OF THE NEW PLANT

The present invention comprises a new and distinct cultivar of *Diascia*, botanically known as *Diascia barberae*, and hereinafter referred to by the cultivar name 'Dala Rossa'. The new cultivar originated from a hybridization made in 2002 in Andijk, The Netherlands. The female parent is a proprietary *Diascia* plant designated 'DSY-3-1' (unpatented), having pink flowers and the male parent is a proprietary *Diascia* plant designated 'DSY-18-1' (unpatented), having a deep rose flower color. The seeds produced by the hybridization were sown in November 2002, and the resulting seedlings were selected in February 2003. A single plant selection was chosen for further evaluation and for asexual propagation in the summer of 2003.

The new cultivar was created in 2002 in Andijk, The Netherlands and has been asexually reproduced repeatedly by vegetative cuttings and tissue culture micropropagation in Andijk, The Netherlands over a two-year period. The plant has also been trialed at Gilroy, Calif., and Andijk, The Netherlands. The present invention has been found to retain its distinctive characteristics through successive asexual propagations.

Plant Breeder's Rights for this cultivar were applied for in Europe on Jan. 24, 2005 and in Canada on Mar. 31, 2005.

SUMMARY OF THE INVENTION

The following are the most outstanding and distinguishing characteristics of this new cultivar when grown under normal horticultural practices in Gilroy, Calif. and Andijk, The Netherlands.

1. Medium-sized rose-pink flowers with reddish markings on the inner part of the corolla;

2. Medium-green foliage with relatively narrow leaves;
3. A medium-sized, semi-upright plant habit; and
4. A tight and well-branched plant habit.

DESCRIPTION OF PHOTOGRAPH

This new *Diascia* plant is illustrated by the accompanying photograph which shows blooms, buds, and foliage of the plant in full color; the colors shown are as true as can be reasonably obtained by conventional photographic procedures. The photograph is of three 6-month-old plants grown in a greenhouse with natural light in spring trial setting.

The accompanying photograph shows blooms, buds, mature foliage, and plant habit; the inset shows mature inflorescences and buds.

DESCRIPTION OF THE NEW CULTIVAR

The following detailed descriptions set forth the distinctive characteristics of 'Dala Rossa'. The data which define these characteristics were collected from asexual reproductions carried out in Hillscheid, Germany. The plant history was taken on seven-month-old plants grown, 3 plants each, in 35-cm-diameter baskets (capable of holding 5-liters of soil) in an outdoor trial field under poly-cover rain protection. Color readings were taken under natural light. Color references are primarily to The R.H.S. Colour Chart of The Royal Horticultural Society of London (R.H.S.) (2001 edition).

DESCRIPTION OF THE NEW PLANT

Classification:
*Family.*—Scrophulariaceae.
*Botanical name.*—*Diascia barberae* Hook.

Parentage:

*Female parent.*—'DSY-3-1' a proprietary pink-flowered *Diascia* plant (unpatented).

*Male parent.*—'DSY-18-1' a proprietary deep-rose-flowered *Diascia* plant (unpatented).

Growth:

*Form and growth habit.*—Upright and outwardly spreading with ascending to semi-trailing branches; very well branched and relatively tight.

*Height.*—15 cm (from top of soil) for 7-month-old plants to 30 cm (total vertical height) of a plant in a hanging basket.

*Width.*—75–80 cm.

*Spread* (*including flowers*).—55 cm, from the base of the main stem to the tips of the branches.

*Time to produce a finished flowering plant.*—10 weeks for a 5-inch pot.

*Outdoor plant performance.*—Plant in full sun; is free-flowering through the summer; has some heat tolerance; use in mixed container planting or mass planting in a bed.

*Time to initiate and develop roots.*—About 20 days in the spring.

*Root description.*—Fibrous and freely branching.

Leaves:

*Arrangement.*—Single and opposite.

*Shape.*—Cordate.

*Apex.*—Acute to obtuse.

*Base.*—Truncate to weakly cordate.

*Margin.*—Weakly serrate.

*Immature.*—Color: Upper surface: RHS 143A. Lower surface: RHS 138B.

*Mature* (*fully expanded*).—Length: 1.9 cm. Width: 1.4 cm. Color: Upper surface: RHS 137B. Lower surface: RHS 138B.

*Venation.*—Type: Pinnate. Color: RHS 144B.

*Texture.*—Smooth and glabrous.

*Petiole.*—Length: 0.2–0.3 cm. Width: 0.2 cm. Color: RHS 144A.

Stems:

*Length.*—40 cm without the inflorescence.

*Diameter.*—0.3–0.4 cm as measured in the middle (is square not round).

*Internode length.*—Approximately 1.5 cm.

*Color.*—RHS 143A.

*Texture.*—Appears glabrous.

*Anthocyanin.*—Absent.

Flower bud:

*Shape.*—Round and somewhat flattened.

*Diameter.*—0.6 cm.

*Length.*—0.45 cm.

*Color* (*at tight bud*).—RHS N74D.

Inflorescence:

*Inflorescence type.*—Terminal raceme with flowers in an alternate arrangement.

*Blooming habit.*—Continuously.

*Quantity of inflorescences per plant.*—100.

*Lastingness of individual blooms on the plant.*—3–4 days.

*Fragrance.*—None.

*Inflorescence length.*—10–12 cm.

*Penduncle.*—Color: RHS 143A. Length: 10.0–11.5 cm. Diamter: 0.2 cm or less. Texture: Covered with fine pubescence.

Flower:

*Type.*—Single, zygomorphic; 5-lobes fused at the base.

*Quantity* (*per raceme*).—3–5 open flowers at the same time with a total of about 20 flowers and buds at various stages of development.

*Shape.*—Salver-shaped.

*Length.*—2.1 cm.

*Depth.*—0.5 cm.

*Width.*—2.0 cm.

*Color.*—Upper surface: RHS 55A. Lower surface: RHS 54B. Corolla (inside color): RHS 54A; upper petals have a patch of RHS 13A (yellow) at the base.

*Petals* (*lobes*).—Quantity: 5. Arrangement: Two upper lobes (mainly fused) with two lateral lobes and one lower lobe. Apex: Rounded. Base: Fused. Margin: Entire. Texture: Smooth.

*Upper lobes, size.*—Length (from the Corolla opening): 0.5 cm. Width: 1.0 cm.

*Lateral lobes, size.*—Length (from the Corolla opening): 0.6 cm. Width: 0.8 cm. Spur: Shape: Funnel-shaped. Length: 0.7 cm. Diameter: 0.3 cm at the flower end. Color: RHS 53D (purple).

*Lower lobe.*—Length (from the Corolla opening): 1.1 cm. Width: 1.4 cm.

*Sepals.*—Quantity: 5. Color: RHS 143A. Length: 0.2 cm. Width: 0.1 cm. Shape: Deltoid to lanceolate. Apex: Acute. Base: Fused. Anthocyanin: Absent. Texture: Rough, pubescent.

*Pedicels.*—Color: RHS 144A. Length: 1.3–1.5 cm. Diameter: 0.1 cm. Texture: Covered with very fine pubescence.

Reproductive organs:

*Stamens.*—Quantity: 4; coherent, arching towards and somewhat twisting around the pistil. Filament: Color: RHS 60B (purple). Length: 0.3–0.4 cm. Diameter: 0.1 cm. Anther color: RHS 13D (pale yellow). Pollen amount: Abundant. Pollen color: RHS 13A (yellow).

*Pistils.*—Quantity: 1. Length: 0.4 cm. Stigma color: RHS 143D (light-green). Style color: RHS 145B.

Fruit and seed set: Has not been observed.

Disease and insect resistance: Has not been observed.

COMPARISON WITH PARENTAL AND COMMERCIAL CULTIVARS

'Dala Rossa' differs from the female parent, proprietary *Diascia* plant 'DSY-3-1' (unpatented), in that 'Dala Rossa' has a deep rose flower color while 'DSY-3-1' has a pink flower color. Additionally, 'Dala Rossa' is more free flowering than 'DSY-3-1'.

'Dala Rossa' differs from the male parent, proprietary *Diascia* plant 'DSY-18-1' (unpatented), in that 'Dala Rossa' has a lighter rose flower color, is more floriferous, and has a more compact plant habit than 'DSY-18-1'.

'Dala Rossa' differs from the commercial cultivar 'Diastu' (U.S. Plant Pat. No. 13,949) in that 'Dala Rossa' has larger flowers and a more upright plant habit than 'Diastu'.

I claim:

1. A new and distinct cultivar of *Diascia* plant as shown and described herein.

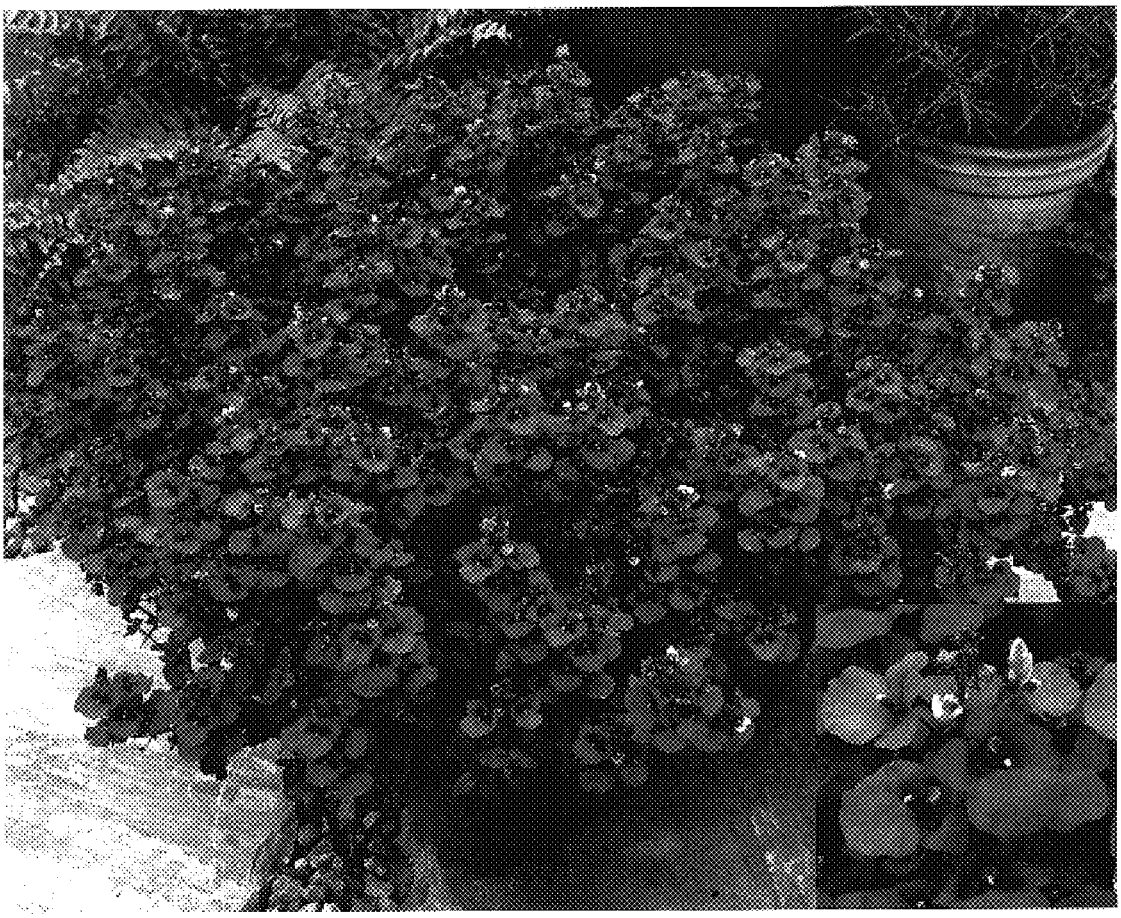

* * * * *